United States Patent [19]

Inoue et al.

[11] 4,110,466
[45] Aug. 29, 1978

[54] OXYINDOLE COMPOUND

[75] Inventors: Satoru Inoue, Nishinomiya; Tamon Uematsu, Toyonaka; Norihisa Yamashita, Takarazuka, all of Japan

[73] Assignee: Sumitomo Chemical Company, Limited, Japan

[21] Appl. No.: 820,942

[22] Filed: Aug. 1, 1977

[30] Foreign Application Priority Data

Aug. 10, 1976 [JP] Japan .................................. 51-95877
Oct. 14, 1976 [JP] Japan ................................ 51-123628

[51] Int. Cl.² ............................................. A01N 9/22
[52] U.S. Cl. ........................... 424/274; 260/326.11 R
[58] Field of Search ................ 260/326.11 R; 424/274

[56] References Cited

U.S. PATENT DOCUMENTS 3,917,838  11/1975  Bass et al. ............................. 424/258

FOREIGN PATENT DOCUMENTS 2,159,363  6/1973  Fed. Rep. of Germany.

OTHER PUBLICATIONS

Sumpter et al.; J.A.C.S. 67(1945) 1656–1658.
Wenkert et al.; J.A.C.S. 78(1956) 797–801.
Cook et al.; J.C.S. 568–569 (1954).
Loudon et al.; J.C.S. (1955) 739–744.

*Primary Examiner*—Allen J. Robinson
*Attorney, Agent, or Firm*—Wenderoth, Lind & Ponack

[57] ABSTRACT

An agricultural and horticultural microbicidal composition which comprises as an active ingredient a compound represented by the formula:

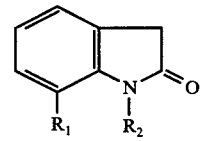

wherein $R_1$ is a methyl or ethyl group, halogen atom or methoxy group and $R_2$ is a methyl or ethyl group, and an inert carrier, which shows high microbicidal activities against phyto-pathogenic microorganisms without any material toxicity to mammals, fishes and crops.

6 Claims, No Drawings

OXYINDOLE COMPOUND

The present invention relates to an agricultural and horticultural microbicidal composition comprising as an active ingredient an oxindole compound of the formula (I):

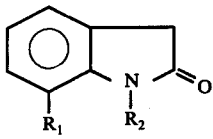

wherein $R_1$ is a methyl or ethyl group, a halogen atom or methoxy group and $R_2$ is a methyl or ethyl group.

As a result of our extensive studies on oxindole compounds, we have found that a class of compounds represented by the abovementioned formula (I) (hereinafter called as present compounds) exhibit high microbicidal activities against various phyto-pathogenic microorganisms.

Recently, from the force of operational circumstances, earnest desire is directed to the finding of such agricultural and horticultural chemicals that have higher activities against various phyto-pathogenic microorganisms, which is serviceable in the simplification of work, i.e. simultaneous control of more than two injurious diseases, and are employable in various ways in various forms as, for example, foliar application in the form of dust, emulsifiable concentrate, wettable powder and fine granule, submerged application in the form of dust, emulsifiable concentrate, wettable powder, water-surface-spreading oil based liquid and granule, soil application and the like. Environmental pollution is also a pressing problem and the least toxicity to mammals and fishes and easy decomposition are likewise the conditions to be desired in these chemicals.

With due regard to the above, the inventors have prosecuted the study for years and found that though 1- or 7-substituted oxindoles posses a certain level of microbicidal activities, the present compounds having substituents at both 1 and 7 positions do exhibit higher activities against various phyto-pathogenic microorganisms causing serious damages to agricultural crops, as Phycomycetes, Ascomycetes, Basidiomycetes, Fungi Imperfecti and other bacteria. These compounds are, inter alia, particularly useful for the control of rice blast and Helminthosporium leaf spot which are serious diseases in a rice crop, and are applicable in various ways in various forms including foliar application, submerged application and soil application, to obtain a higher level of control effect. Since the present compounds have good vapor actions, it is also possible to adopt an application making the most of this particular property thereinto. To our great surprise, the present compounds can produce instantaneous effects as well as long-lasting residual effects which are never found in any of the existing rice blast controlling agents used by foliar, submerged and soil applications. These facts are totally unexpected over the actions and properties of heretofore known rice blast controlling agents, and the present invention has been made on the basis of these novel findings.

On the other hand, the toxicities of the present compounds toward warm-blooded animals as mice, rats, dogs, and chickens, and fishes as carp, killifishes and the like are very low and the residual effects in crops are almost negligible in substance. Thus, the invented compositions are ideal one causing no environmental pollution problem and showing very effective control of phyto-pathogenic fungi.

Among the compounds represented by the generic formula (I), there, indeed, are some known members, but their agricultural chemical uses have never been known. For example, 1-methyl-7-chloroxindole and 1-ethyl-7-chloroxindole are shown as an intermediate compound in German Pat. No. 2159363, but no biological activities of these compounds are given therein. 1,7-Dimethyl-oxindole is described as an intermediate compound in J.C.S. 568–569 (1954) but this publication is silent about the biological activities thereof. The latter is also described as an intermediate in German Pat. No. DT-159363, but the biological activities of this compound are likewise unknown.

In order to prepare the present compounds, N-chloroacetyl derivatives of the corresponding N-alkylanilines are, as in a conventional way (Stolle; J. Prakt. Chem. [2] 128. 1 (1930)) for the synthesis of oxindole derivative, heated with aluminium chloride at 160° – 220° C. for one hour, and thereafter, the reaction mixture is treated with a diluted hydrochloric acid to separate the objective compound therefrom. The present compounds may also be prepared by conducting an alkylation at 1-position of the oxindole derivatives obtained via isatin derivatives as described in Bull. Soc. Chim. Fr. 1968(I) 390–394. 1-Methyl-7-methoxy oxindole, the present compound No. 6 in the Table hereinafter stated, may be prepared by the methods described in J.C.S. 739–744 (1955) and in Tetrahedron 24, 6093–6109. Compound No. 5 was prepared, as in the case of compounds No. 3 and No. 4, according to a conventional synthesis of oxindole derivatives (Stolle; J. Prakt. Chem. [2] 128. 1 (1930)), by heating N-methyl-N-chloroacetyl-o-bromoaniline with aluminium chloride at 160° – 220° C. These compounds may also be prepared by subjecting 7-substituted oxindole obtained by the ring closure of N-chloroacetyl-o-substituted aniline as stated hereinabove, to N-alkylation in an appropriate solvent with an appropriate alkylating agent in the presence of base.

The later described reference compound No. 1 was prepared by first synthesizing 7-ethyl isatin by the method of S. Geiger, Bull. Soc. Chim. Fr. 1968 (I) 390–394, and then conducting N-methylation in benzene with NaH and methyliodide. The reference compound No. 3 was prepared by subjecting N-methyl-N-chloroacetyl-p-toluidine to a ring closure with aluminium chloride in a conventional method.

Examples of the present compounds obtained by the abovementioned processes and reference compounds are shown below. It should be noted, however, that the present invention can never be limited only to these embodized members.

| compound No. | structure | physical constant |
|---|---|---|
| present compounds | | |
| No. 1 | (structure with $CH_3$, $CH_3$) | M.P. 119 – 120° C. |

-continued

| compound No. | structure | physical constant |
|---|---|---|
| No. 2 | benzene ring fused to N(CH₃)-C=O ring with C₂H₅ substituent | N-methylation of NH deriv. obtained by the method of S.Geiger, Bull. Soc. Chim. Fr. 1968 (I) 390–394 M.P. 57 – 58° C. |
| No. 3 | benzene ring fused to N(CH₃)-C=O ring with Cl substituent | M.P. 120 – 123° C. |
| No. 4 | benzene ring fused to N(C₂H₅)-C=O ring with Cl substituent | M.P. 101 – 102° C. |
| No. 5 | benzene ring fused to N(CH₃)-C=O ring with Br substituent | M.P. 133 – 135° C. |
| No. 6 | benzene ring fused to N(CH₃)-C=O ring with OCH₃ substituent | M.P. 102° C. | reference compounds

| | | |
|---|---|---|
| No. 1 | benzene ring fused to N(CH₃)-C=O ring | Stolle, J. Prakt. Chem. (2) 128. 1 (1930) Stolle M.P. 88 – 90° C. |
| No. 2 | benzene ring fused to NH-C=O ring with C₂H₅ substituent | Via isatin derivative, S. Geiger, Bull. Soc. Chim. Fr. 1968(I) 390–394 M.P. 155 – 156° C. |
| No. 3 | CH₃-substituted benzene ring fused to N(CH₃)-C=O ring | M.P. 104 – 105° C. |
| No. 4 | benzene ring fused to NH-C=O ring with CH₃ substituent | S. Geiger, Bull. Soc. Chim. Fr. 1968(I) 390–394 M.P. 208° C. |
| No. 5 | CH₃-substituted benzene ring fused to N(CH₃)-C=O ring with Cl substituent | E. Wenkert, J.A.C.S. 78 (1956) 797–801 M.P. 60 – 61° C. |

-continued

| compound No. | structure | physical constant |
|---|---|---|
| No. 6 | Br-substituted benzene ring fused to NH-C=O ring | W.C. Sumpter, J.A.C.S. 67 (1945) 1656–1658 M.P. 260° C. |
| No. 7 | di-Br-substituted benzene ring fused to N(CH₃)-C=O ring | W.C. Sumpter, J.A.C.S. 67 (1945) 1656–1658 M.P. 211 – 212° C. |
| No. 8 | benzene ring fused to NH-C=O ring with OCH₃ substituent | A.H. Beckett, Tetrahedron (1968) 24, 6093–6109 M.P. 148 – 149° C. |
| No. 9 | benzene ring fused to N-C=O ring with propyl substituent | U.S. Pat. No. 3917838 |

In the following description, each individual compound specifically named up should be referred to the above-mentioned Table.

Though the present compounds may be used as agricultural and horticultural microbicidal agent as they are, they may be prepared in any formulation customarily used including dust, granule, fine granule, wettable powder, emulsifiable concentrate, oily product and the like. These formulations are preferably selected according to the object of application.

In preparing the abovesaid formulations, an appropriate solid or liquid carrier may be used. As a solid carrier, use is made of fine powder or granule of botanical carrier as flour, tobacco stalk powder, soybean powder, walnut shell powder, wood powder, saw dust, bran, bark powder, cellulose powder, and vegetable extract residue; fibrous material as paper, corrugated cardboard and old rags; synthesized plastic powders; clays as Raolin, bentonite, and fuller's earth; talcs; other inorganic minerals as pyrophyllite, sericite, pumice, sulfur powder and active carbon and chemical fertilizers as ammonium sulphate, ammonium phosphate, ammonium nitrate, urea and ammonium chloride. As a liquid carrier, mention is made of water; alcohols as methyl alcohol and ethyl alcohol; ketones as acetone and methyl ketone; ethers as ethyl ether, dioxan, cellosolve and tetrahydrofuran; aromatic hydrocarbons as benzene, toluene, xylene and methyl naphthalene; aliphatic hydrocarbons as gasoline, kerosene and lamp oil; esters; nitriles, acidamides as methyl formamide and dimethyl acetamide; and halogenated hydrocarbons as dichloroethane and carbon tetrachloride. Examples of surfactant used may include alkyl sulfuric ester alkyl sulphonate, alkylaryl sulphonate, polyethyleneglycolethers and polyhydric alcohol esters. Examples of sticker and dispersant used in the present invention may include casein, gelatine, starch powder, CMC, gum arabic, alginic acid, lignin, bentonite, molasses, polyvinyl alcohol, pine oil and agar. As a stabilizer, use is made of such members as PAP (isopropyl acid phosphates mixture), TCP (tricresyl phosphate), tolu oil, epoxidized oil, various surfactants and various fatty acids and esters thereof.

The present compositions may be used in admixture with other pesticide preparations. Such preparations may include Kasugamycin, Polyoxins, Validamycin, 2,6-dichloro-4-nitroaniline, zinc ethylene bisdithiocarbamate, 2,4-dichloro-6-(o-chloroanilino)-S-triazine, O,O-dimethyl O-(3-methyl-4-nitrophenyl) phosphorothioate, methyl arsonic iron, 1,2-bis-(3-ethoxycarbonyl-2-thioureido )-benzene, 1,2-bis(3-methoxycarbonyl-2-thioureido)-benzene, methyl 1-(butyl carbamoyl)-2-benzimidazoylcarbamate, tetrachloroisophthalonitrile, EPN, Diazinone, Malathion, BPMC, Chlorphenamidine, DCPA, Benthiocarb, CAT, O,O-diisopropyl s-benzyl thiophosphate, O-ethyl S,S-diphenyl thiophosphate, diisopropyl 1,3-dithiolan-2-ylidene-malonte, O,O-dimethyl S-(N-methyl carbamoylmethyl) dithiophosphate, O,O-dimethyl O-(p-cyanophenyl) thiophosphate, O-ethyl O-p-cyanophenyl phenylphosphonothioate, 2-methoxy-4H-1,3,2-benzodioxaphospholine-2-sulfide and the like. Admixture with such preparation would never cause the decrease in the activities of each ingredient included. Therefore, by selecting an appropriate combination of the present composition with these preparations, it is possible to control more than two agricultural pests and weeds in a single operational work. The present compositions may also be used in admixture with other nematocides, acaricides and even with fertilizers.

The invention shall be now more minutely explained in the following Formulation Examples and working Examples. It should be noted, however, that the present invention can never be limited only to the embodied compounds, additives and blending ratio, and they are variable in wider range respectively. Furthermore, the following examples illustrate only a part of the test results obtained and the present compositions can be used as agricultural microbicidal agents in various applications in various forms, without leaving the spirit and the scope of the present invention.

Formulation Example 1 Dust 2.5 Parts of the present compound No. 1 and 97.5 parts of clay were pulverized and mixed well to obtan a dust formulation containing 2.5% active ingredient. This may be used as it is or in admixture with soil.

Formulation Example 2 Dust 0.1 Part of the present compound No. 1 and 99.9 parts of clay were pulverized and mixed well to obtain a dust formulation containing 0.1% of active ingredient,. This may be used as it is or in admixture with soil.

Formulation Example 3 Emulsifiable concentrate

25 Parts of the present compound No. 3 were mixed with 55 parts of xylol and 20 parts of Solpol 2120 (Trade mark of Toho Chemical Co.) to obtain an emulsifiable concentration containing 25% of active ingredient. Before use, this may be diluted with water, or this concentrate may be used as it is.

Formulation Example 4 Wettable powder

90 Parts of the present compound No. 1, 5 parts of wetting agent (alkyl benzene sulphonate series) and 5 parts of white carbon were pulverized and mixed well to obtain a wettable powder containing 90% of active ingredient. This may be used after dilution with water or in admixture with soil.

Formulation Example 5 Granule

The acetone solution of 10 parts of the present compound No. 3 were blown against 90 parts of bentonite of 16 - 32 mesh-size and soaked therein and dried up to obtain granules containing 10% of active ingredient. This formulation may be used as it is or after dilution with water.

Formulation Example 6 Floating type granule

The acetone solution of 10 parts of the present compound No. 1 were blown against 85 parts of pumice of 16 - 32 mesh-size and soaked therein and dried up. Thereafter, 5 parts of liquid paraffin were blown against the granules and soaked to obtain floating type granules containing 10% of active ingredient. This formulation may be used as it is.

Formulation Example 7 Coating type granule

The mixture of fine divided powder of 10 parts of the present compound No. 3 and 1 part of white carbon were mixed with the mixture of 86 parts of silica sand and 3 parts of 10% solution of PVA (polyvinylalcohol) in water to obtain coating type granules containing 10% of active ingredient. This may be used as it is.

Formulation Example 8 Granule

10 Parts of the present compound No. 1 and 1 part of white carbon were mixed and pulverized and then were mixed with 30 parts of bentonite, 1 part of calcium lignin sulfonate, 0.1 part of sodium lauryl sulfate and 57.9 parts of clay and the mixture was added with water and kneaded well.

This mixture was extruded out through a screen having apertures (0.7 mm. in diameter) and the granules obtained were dried. The content of active ingredient was 10%. This may be used after dilution with water or as it is.

Formulation Example 9 Water-surface-spreading oil based liquid

1 Part of the present compound No. 1 was mixed with 10 parts of polyoxypropyleneglycol monoether and 89 parts of kerosene to obtain a water-surface spreading oil based liquid containing 1% of active ingredient. The formulation may be used as it is.

The following examples show typical experimental data demonstrating the specific properties of the present compositions, i.e. simultaneous control of more than two phyto-pathogenic microorganisms (easy control operation) and various applications including foliar application, submerged application, soil application and the like.

EXAMPLE 1 rice blast controlling effect - foliar application (preventive effect)

To rice plants (Kinki No. 33, 4 - 5 leaves stage) cultivated in pots of 9 cm. in diameter, test compounds in the form of emulsifiable concentrates prepared according to the method described in Formulation Example 3 were diluted with water and spray-applied by means of spray gun in an amount of 15 ml/pot. After one day from said spraying, a spore suspension of *Pyricularia oryzae* was spray-inoculated onto the plants and the inoculated pots were placed in a constant temperature room maintained at 24° – 26° C. and a humidity of more than 90%. After 4 days standing, disease severity was determined by the percentage of infected leaf area and examined the control effect. The results are shown in the following Table 1. Disease control was calculated by using the following equation.

Disease severity = $\frac{\Sigma \text{ (infection index} \times \text{number of leaves)}}{8 \times \text{total number of leaves observed}} \times 100$

| infection index | % of leaf area infected |
| --- | --- |
| 0 | 0% (none) |
| 1 | less than 10% |
| 2 | 10% to less than 25% |
| 4 | 25% to less than 55% |
| 8 | 55% to 100% |

Disease control (%) = $(1 - \frac{\text{disease severity in treated plot}}{\text{disease severity in untreated plot}}) \times 100$ Table 1

| test compound | concentration of active ingredient (ppm) | disease control (%) |
| --- | --- | --- |
| present compound | | |
| No. 1 | 100 | 100 |
| No. 2 | 100 | 100 |
| No. 3 | 100 | 100 |
| No. 4 | 100 | 100 |
| No. 5 | 100 | 100 |
| No. 6 | 100 | 100 |
| reference compound | | |
| No. 1 | 100 | 85 |
| No. 2 | 100 | 84 |
| No. 3 | 100 | 5 |
| No. 4 | 100 | 90 |
| No. 5 | 100 | 0 |
| No. 6 | 100 | 10 |
| No. 7 | 100 | 20 |
| No. 8 | 100 | 85 |
| commercial fungicide* | 200 | 81 |
| untreated | — | 0 |

*O,O-diisopropyl S-benzyl phosphorothiolate (48% E.C.)

EXAMPLE 2 rice blast controlling effect - foliar application (residual effect)

To rice plants (Kinki No. 33, 4 – 5 leaves stage) cultivated in pots of 9 cm. in diameter, test compounds in the form of emulsifible concentrates prepared as in Formulation Example 3 were diluted with water and applied by means of spray gun in an amount of 15 ml. per pot. After 4 days from said spraying, a spore suspension of Pyricularia oryzae was spray-inoculated onto the plants and the inoculated pots were placed in a constant temperature room maintained at 24° – 26° C. and a humidity of more than 90%. After 4 days standing, disease severity was determined by the percentage of infected leaf area and examined control effects of the tested compounds. The results are shown in the following Table 2. The calculation of disease severity and of control % were carried out as in Example 1.

Table 2

| test compound | concentration of active ingredient (ppm) | disease control (%) |
| --- | --- | --- |
| present compound | | |
| No. 1 | 200 | 100 |

Table 2-continued

| test compound | concentration of active ingredient (ppm) | disease control (%) |
| --- | --- | --- |
| No. 2 | 200 | 100 |
| No. 3 | 200 | 100 |
| No. 4 | 200 | 100 |
| No. 5 | 200 | 100 |
| No. 6 | 200 | 100 |
| reference compound | | |
| No. 1 | 200 | 22 |
| No. 2 | 200 | 25 |
| No. 3 | 200 | 0 |
| No. 4 | 200 | 30 |
| No. 5 | 200 | 0 |
| No. 6 | 200 | 0 |
| No. 7 | 200 | 0 |
| No. 8 | 200 | 25 |
| No. 9 | 200 | 46 |
| commercial fungicide* | 200 | 40 |
| untreated | — | 0 |

*O-ethyl S,S-diphenyl dithiophosphate (30% E.C.)

EXAMPLE 3 rice blast controlling effect - submerged application

To rice plants (Kinki No. 33, 5 – 6 leaves stage) cultivated under flooded conditions in Wagner pots (1/5000 are), test compounds formulated in granules as in Formulation Example 5 were submerged-applied. The test granules were scattered uniformly on the surface of water in an amount equivalent to 500 g. of active ingredient per 10 ares, and the pots were maintained at a depth of 4 – 5 cm. for defined period of time before inoculation with test microorganisms, in a green house. After 4 days and 30 days from said medication, a spore suspension of Pyricularia oryzae was spray-inoculated onto the plants and the inoculated pots were placed in a constant temperature room maintained at 24° – 26° C. and a humidity of more than 90%. After 4 days standing, disease severity was examined by observing the percentage of infected leaf area and determined the control effects as in Example 1. The results are shown in the following Table 3.

Table 3

| | disease control (%) | |
| --- | --- | --- |
| test compound | treated at 4 days before inoculation | treated at 30 days before inoculation |
| present compound | | |
| No. 1 | 100 | 100 |
| No. 2 | 100 | 100 |
| No. 3 | 100 | 100 |
| No. 4 | 100 | 88 |
| No. 6 | 100 | 80 |
| commercial fungicide* | 86 | 31 |
| untreated | 0 | 0 |

*O,O-diisopropyl S-benzyl phosphorothioate (17% granule)

EXAMPLE 4 rice blast controlling effect - soil application test

To rice plants (Kinki No. 33, 5 – 6 leaves stage) cultivated in Wagner pots (1/5000 are), test compounds in the form of emulsifiable concentrates formulated as in Formulation Example 3 were applied to soil. Each emulsifiable concentrate was diluted with water and applied on the surface of soil in an amount equivalent to 500 g. active ingredient per 10 ares. After 4 days and 30 days, a spore suspension of Pyricularia oryzae was spray-inoculated onto the plant and the inoculated pots were placed in a constant temperature room maintained at 24° – 26° C. and a humidity of more than 90%. After 4 days standing, disease severity and control effect were determined as in Example 1. The results are shown in the following Table 4.

Table 4

| test compound | disease control (%) | |
|---|---|---|
| | treated at 4 days before inoculation | treated at 30 days before inoculation |
| present compound | | |
| No. 1 | 100 | 100 |
| No. 2 | 100 | 97 |
| No. 3 | 100 | 100 |
| No. 4 | 100 | 45 |
| No. 6 | 95 | 30 |
| commercial fungicide* | 90 | 14 |
| untreated | 0 | 0 |

*O,O-diisopropyl S-benzyl phosphorothiolate (48% E.C.)

EXAMPLE 5

Helminthosporium leaf spot controlling effect - foliar application test (preventive effect)

To rice plants (Kinki No. 33, 4 – 5 leaves stage) cultivated in pots (9 cm. in diameter, 4 plants per pot), test compounds in the form of emulsifiable concentrate prepared as in Formulation Example 3 were diluted with water and applied by means of spray gun in an amount of 15 ml. per pot. After one day from said spraying, mycerial disk (5 mm. in diameter) of *Helminthosporium sigmoideum* cultured in PSA medium was attached to the sheath portion of each stem, and the inoculated pots were placed in a constant temperature room maintained at 28° C. After 4 days standing, disease severity was determined by measuring the infected sheath length and using the following equation.

Disease severity = $\frac{\Sigma \text{ (infection index} \times \text{ number of stems)}}{3 \times \text{ total number of stems observed}} \times 100$

| infection index | infected sheath length |
|---|---|
| 0 | 0 (none) |
| 1 | slightly observed, but negligible |
| 2 | less than 1 cm. |
| 3 | more than 1 cm. |

The control effect was determined as in Example 1.

Table 5

| test compound | concentration of active ingredient (ppm) | disease control (%) |
|---|---|---|
| present compound | | |
| No. 1 | 500 | 100 |
| No. 2 | 500 | 90 |
| No. 3 | 500 | 100 |
| No. 4 | 500 | 92 |
| No. 6 | 500 | 95 |
| commercial fungicide* | 500 | 88 |

Table 5-continued

| test compound | concentration of active ingredient (ppm) | disease control (%) |
|---|---|---|
| untreated | — | 0 |

*O-ethyl S,S-diphenyl dithiophosphate (30% E.C.)

As described hereinabove, the characteristic features of the present composition reside in the points that they are very effective against more than 2 pathogenic fungi, and can be used in various forms including formulations suitable for use in foliar, submerged and soil applications and that their controlling effects are instantaneously and also last a longer duration. Among the present compounds having substituents at 1- and 7-positions of oxindole ring, preference is given to 1,7-dimethyl oxindole and 1-methyl-7-chloroxindole because of their outstanding controlling effects.

What we claim is:

1. A method for controlling or preventing plant diseases caused by phytopathogenic fungi, which comprises applying to said fungi a fungicidally effective amount of a fungicidal composition which comprises a compound represented by the formula:

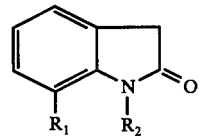

wherein $R_1$ is methyl, ethyl, chlorine, bromine or methoxy and $R_2$ is methyl or ethyl, and an inert carrier therefor.

2. The method according to claim 1, wherein the phytopathogenic fungus is *Pyricularia oryzae*.

3. The method according to claim 1, wherein the phytopathogenic fungus is *Helminthosporium sigmoideum*.

4. A method for controlling phytopathogenic fungi, which comprises applying a fungicidally effective amount of a compound of the formula

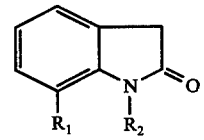

wherein $R_1$ is methyl, ethyl, chlorine, bromine or methoxy and $R_2$ is methyl or ethyl, to the phytopathogenic fungi.

5. The method according to claim 4 wherein the phytopathogenic fungi is *Pyricularia oryzae*.

6. The method according to claim 4 wherein the phytopathogenic fungi is *Helminthosporium sigmoideum*.

* * * * *